(12) United States Patent
Bosua (10) Patent No.: US 11,529,077 B1
(45) Date of Patent: Dec. 20, 2022

(54) HIGH PERFORMANCE GLUCOSE SENSOR

(71) Applicant: Know Labs, Inc., Seattle, WA (US)

(72) Inventor: Phillip Bosua, Seattle, WA (US)

(73) Assignee: KNOW LABS, INC., Seattle, WA (US)

(*) Notice: Subject to any disclaimer, the term of this patent is extended or adjusted under 35 U.S.C. 154(b) by 0 days.

(21) Appl. No.: 17/664,322

(22) Filed: May 20, 2022

Related U.S. Application Data (63) Continuation of application No. 17/662,102, filed on May 5, 2022.

(51) Int. Cl.
*A61B 5/145* (2006.01)
*G16H 20/17* (2018.01)
*A61B 5/0507* (2021.01)

(52) U.S. Cl.
CPC ........ *A61B 5/14532* (2013.01); *A61B 5/0507* (2013.01); *G16H 20/17* (2018.01)

(58) Field of Classification Search
CPC ... A61B 5/14532; A61B 5/0507; G16H 20/17
See application file for complete search history.

(56) References Cited

U.S. PATENT DOCUMENTS

| | | | |
|---|---|---|---|
| 4,202,000 A | 5/1980 | Carballes | |
| 8,223,021 B2 | 7/2012 | Goodnow et al. | |
| 8,882,670 B2 | 11/2014 | Hancock | |
| 9,198,607 B2 | 12/2015 | Fischer | |
| 9,864,024 B2 | 1/2018 | Vester | |
| 10,149,629 B2 | 12/2018 | Szczepaniak et al. | |
| 10,258,268 B2 | 4/2019 | Roblyer et al. | |
| 10,478,101 B1 | 11/2019 | Cespedes et al. | |
| 10,548,503 B2 | 2/2020 | Bosua | |
| 10,617,296 B2 | 4/2020 | Sloan et al. | |
| 10,912,500 B2 | 2/2021 | Poeze et al. | |
| 10,956,950 B2 | 3/2021 | Al-Ali et al. | |
| 11,031,970 B1 | 6/2021 | Bosua | |

(Continued)

FOREIGN PATENT DOCUMENTS

| | | |
|---|---|---|
| EP | 3146898 B1 | 11/2018 |
| EP | 3981329 A1 | 4/2022 |

(Continued)

OTHER PUBLICATIONS

Hanna, J. et al., "Noninvasive, wearable, and tunable electromagnetic multisensing system for continuous glucose monitoring, mimicking vasculature anatomy," Science Advances, 6, eaba5320, 2020 (11 pages).

(Continued)

*Primary Examiner* — Eric J Messersmith
(74) *Attorney, Agent, or Firm* — Hamre, Schumann, Mueller & Larson, P.C.

(57) ABSTRACT

A highly accurate glucose sensor that detects glucose by transmitting and receiving sensing signals in a radio or microwave frequency range of the electromagnetic spectrum is provided. The glucose sensor has at least two antennas at least one of which operates as a transmit antenna to transmit one or more of the sensing signals and at least one of which operates as a receive antenna, and the glucose sensor has a mean absolute relative difference (MARD) value of about 5.0% to about 9.9%, or of about 5.0% to about 7.0%, or of about 5.0%.

19 Claims, 4 Drawing Sheets

(56) References Cited

U.S. PATENT DOCUMENTS

| | | |
|---|---|---|
| 11,033,208 B1 | 6/2021 | Bosua |
| 11,058,317 B1 | 7/2021 | Bosua |
| 11,058,331 B1 | 7/2021 | Bosua |
| 11,063,373 B1 | 7/2021 | Bosua |
| 11,193,923 B2 | 12/2021 | Bosua |
| 11,202,582 B2 | 12/2021 | Verkruijsse et al. |
| 11,223,383 B2 | 1/2022 | Bosua |
| 11,234,619 B2 | 2/2022 | Bosua |
| 11,244,753 B2 | 2/2022 | Haggerty et al. |
| 11,291,374 B2 | 4/2022 | Lee et al. |
| 11,350,830 B2 | 6/2022 | McKenna et al. |
| 11,360,188 B2 | 6/2022 | Leabman |
| 11,367,525 B2 | 6/2022 | Addison et al. |
| 11,389,093 B2 | 7/2022 | Triman et al. |
| 11,426,104 B2 | 8/2022 | Schurman et al. |
| 2003/0036713 A1 | 2/2003 | Bouton et al. |
| 2004/0065158 A1 | 4/2004 | Schrepfer et al. |
| 2004/0127777 A1 | 7/2004 | Ruchti et al. |
| 2004/0133086 A1 | 7/2004 | Ciurczak et al. |
| 2008/0319285 A1 | 12/2008 | Hancock |
| 2009/0275814 A1 | 11/2009 | Watanabe et al. |
| 2010/0041969 A1 | 2/2010 | Beise |
| 2011/0028814 A1 | 2/2011 | Petersen et al. |
| 2013/0289375 A1 | 10/2013 | Fischer |
| 2014/0213870 A1 | 7/2014 | Hsu et al. |
| 2016/0051171 A1 | 2/2016 | Pikov et al. |
| 2017/0095667 A1 | 4/2017 | Yakovlev et al. |
| 2018/0028824 A1 | 2/2018 | Pivonka et al. |
| 2018/0303391 A1 | 10/2018 | Roblyer et al. |
| 2019/0008422 A1 | 1/2019 | Leath et al. |
| 2019/0053741 A1 | 2/2019 | Chaudhry |
| 2019/0104939 A1 | 4/2019 | Costantine et al. |
| 2019/0269853 A1 | 9/2019 | Doyle et al. |
| 2019/0388000 A1* | 12/2019 | Costantine ........... A61B 5/7275 |
| 2020/0054255 A1 | 2/2020 | Conrad et al. |
| 2020/0057163 A1 | 2/2020 | Bromberg |
| 2020/0146584 A1 | 5/2020 | Bosua |
| 2020/0187791 A1 | 6/2020 | Leabman |
| 2020/0187792 A1 | 6/2020 | Leabman |
| 2020/0187793 A1 | 6/2020 | Leabman |
| 2020/0187812 A1 | 6/2020 | Leabman |
| 2020/0187813 A1 | 6/2020 | Leabman |
| 2020/0187814 A1 | 6/2020 | Leabman |
| 2020/0187815 A1 | 6/2020 | Leabman |
| 2020/0187816 A1 | 6/2020 | Leabman |
| 2020/0187817 A1 | 6/2020 | Leabman |
| 2020/0187818 A1 | 6/2020 | Leabman |
| 2020/0187819 A1 | 6/2020 | Leabman |
| 2020/0187820 A1 | 6/2020 | Leabman |
| 2020/0187836 A1 | 6/2020 | Leabman |
| 2020/0187837 A1 | 6/2020 | Leabman |
| 2020/0187867 A1 | 6/2020 | Leabman |
| 2020/0191909 A1 | 6/2020 | Leabman |
| 2020/0191932 A1 | 6/2020 | Leabman |
| 2020/0191933 A1 | 6/2020 | Leabman |
| 2020/0191944 A1 | 6/2020 | Leabman |
| 2020/0191945 A1 | 6/2020 | Leabman |
| 2020/0191947 A1 | 6/2020 | Leabman |
| 2020/0192426 A1 | 6/2020 | Leabman |
| 2020/0192427 A1 | 6/2020 | Leabman |
| 2020/0192428 A1 | 6/2020 | Leabman |
| 2020/0193326 A1* | 6/2020 | Leabman ............... G06N 20/00 |
| 2020/0195197 A1 | 6/2020 | Leabman |
| 2020/0195293 A1 | 6/2020 | Leabman |
| 2021/0186357 A1 | 6/2021 | Bosua et al. |
| 2021/0244308 A1 | 8/2021 | Bosua |
| 2021/0259571 A1 | 8/2021 | Bosua |
| 2021/0259592 A1 | 8/2021 | Bosua |
| 2021/0259593 A1 | 8/2021 | Bosua |
| 2022/0015695 A1 | 1/2022 | Margarito et al. |
| 2022/0031254 A1 | 2/2022 | Al-Ali et al. |
| 2022/0039682 A1* | 2/2022 | Bteich ................... A61B 5/681 |
| 2022/0071505 A1 | 3/2022 | Bosua |
| 2022/0071523 A1 | 3/2022 | Bosua |
| 2022/0071524 A1 | 3/2022 | Bosua |
| 2022/0071527 A1 | 3/2022 | Bosua |
| 2022/0074870 A1 | 3/2022 | Bosua |
| 2022/0074871 A1 | 3/2022 | Bosua |
| 2022/0077602 A1 | 3/2022 | Bosua et al. |
| 2022/0077918 A1 | 3/2022 | Bosua et al. |
| 2022/0192494 A1 | 6/2022 | Leabman |
| 2022/0192531 A1 | 6/2022 | Leabman |
| 2022/0248984 A1 | 8/2022 | Poeze et al. |

FOREIGN PATENT DOCUMENTS

| | | |
|---|---|---|
| JP | 2012125382 | 7/2012 |
| KR | 1020160081740 | 7/2016 |
| WO | 2017163245 | 9/2017 |
| WO | 2019071138 | 4/2019 |
| WO | 2019217461 | 11/2019 |
| WO | 2020006077 | 1/2020 |
| WO | 2020037171 | 2/2020 |
| WO | 2021198045 A1 | 10/2021 |
| WO | 2022026623 A1 | 2/2022 |

OTHER PUBLICATIONS

"Contributes to longer healthy life expectancy with non-invasive vital acquisition sensor," Quantum Operation Co., Ltd., presentation found on Jan. 12, 2021 at https://oi.nttdata.com/program/forum/history/20191118/pdf/03_quantum-op.pdf (14 pages including English translation).

Qiang et al., "Quantitative detection of glucose level based on radiofrequency patch biosensor combined with volume-fixed structures," Biosensors and Bioelectronics 98:357-363, 2017.

Shaker, G. et al., "Non-lnvasive Monitoring of Glucose Level Changes Utilizing a mm-Wave Radar System," IJMHCI, vol. 10, Issue 3 (2018): pp. 10-29.

Lien, J. et al., "Soli: Ubiquitous Gesture Sensing with Millimeter Wave Radar," ACM Trans. Graph., vol. 35, No. 4, Article 142, 19 pages (Jul. 2016).

Stojanovic, R. et al., "An optical sensing approach based on light emitting diodes," Journal of Physics: Conference Series 76 (2007), pp. 1-6.

Rossiter, J. et al., "A novel tactile sensor using a matrix of LEDs operating in both photoemitter and photodetector modes," Proc of 4th IEEE International Conference on Sensors (IEEE Sensors 2005), pp. 994-997.

Freckmann, G. et al., "Mean Absolute Relative Difference of Blood Glucose Monitoring Systems and Relationship to ISO 15197," Journal of Diabetes Science and Technology, 00(0), 2021, pp. 1-7.

Reiterer, F. et al., "Significance and Reliability of MARD for the Accuracy of CGM Systems," Journal of Diabetes Science and Technology, 11(1), 2017, pp. 59-67.

* cited by examiner

HIGH PERFORMANCE GLUCOSE SENSOR

FIELD

This disclosure relates generally to apparatus, systems and methods of detecting an analyte via spectroscopic techniques using an analyte sensor that operates in the radio or microwave frequency range of the electromagnetic spectrum.

BACKGROUND

There is interest in being able to detect and/or measure an analyte within a target. One example is measuring glucose in biological tissue. In the example of measuring glucose in a patient, many current analyte measurement methods are invasive in that they perform the measurement on a bodily fluid such as blood for fingerstick or laboratory-based tests, or on fluid that is drawn from the patient often using an invasive transcutaneous device. There are non-invasive methods that claim to be able to perform glucose measurements in biological tissues. However, many of the non-invasive methods generally suffer from: lack of specificity to the analyte of interest, such as glucose; interference from temperature fluctuations; interference from skin compounds (i.e. sweat) and pigments; and complexity of placement, i.e. the sensing device resides on multiple locations on the patient's body.

SUMMARY

This disclosure relates generally to apparatus, systems and methods of detecting an analyte via spectroscopic techniques using non-optical frequencies such as in the radio or microwave frequency range of the electromagnetic spectrum. An analyte sensor described herein includes a plurality of detector elements (also referred to as antenna elements or antennas) at least one of which can transmit an electromagnetic signal in the radio or microwave frequency range into a target and at least one of which can receive an electromagnetic signal in the radio or microwave frequency range resulting from transmission of the electromagnetic signal. In an embodiment, the detector elements may be part of a common detector array.

The analyte sensor described herein can be used to detect glucose and/or other analyte(s). When used to detect glucose, the sensor can be referred to as a glucose sensor. When used to detect an analyte in general, including glucose and other analytes, the sensor can be referred to as an analyte sensor. The sensor described herein can operate non-invasively whereby the sensor remains completely external to the body from which the glucose or other analyte(s) is sensed. In other embodiments, the sensor can operate in a minimally invasive manner whereby a portion of the sensor pierces the body, the sensor can be invasive whereby the sensor is completely installed in the body, or the sensor can sense glucose or other analyte(s) from a material or fluid that is drawn from and external to the body.

One way to assess the accuracy of a glucose sensor is mean absolute relative difference (MARD). A MARD value of a glucose sensor is determined by comparing the glucose reading of the glucose sensor against a reference glucose reading of a reference glucose sensor. The lower the MARD value, the more accurate the glucose sensor is. The glucose sensor described herein that operates using signals that are in the radio or microwave frequency range is highly accurate. For example, the glucose sensor described herein has a MARD value of about 5.0% to about 9.9%, or a MARD value of about 5.0% to about 7%, or a MARD value is about 5.0%.

In one embodiment, a glucose sensor that transmits and receives sensing signals in a radio or microwave frequency range of the electromagnetic spectrum is provided. The glucose sensor has at least two antennas at least one of which operates as a transmit antenna to transmit one or more of the sensing signals and at least one of which operates as a receive antenna, and the glucose sensor has a MARD value of about 5.0% to about 9.9%, or of about 5.0% to about 7.0%, or of about 5.0%.

In another embodiment, a non-invasive glucose sensor is described that transmits and receives sensing signals in a radio or microwave frequency range of the electromagnetic spectrum to detect glucose in a human or animal body. The non-invasive glucose sensor has at least three antennas at least one of which operates as a transmit antenna to transmit one or more of the sensing signals into the human or animal body and at least one of which operates as a receive antenna, and the non-invasive glucose sensor has an accuracy that is greater than the accuracy of commercially available glucose sensors such as a) a minimally invasive continuous glucose sensor and b) a fingerstick glucose sensor. For example, the glucose sensor described herein can have a MARD value of about 5.0% to about 9.9%, or of about 5.0% to about 7.0%, or of about 5.0%.

The high accuracy of the glucose sensor described herein would permit the described glucose sensor to be used as a standard or reference glucose sensor against which the performance of other glucose sensors, such as minimally invasive CGMs and fingerstick sensors, can be compared to determine their accuracy.

For example, a minimally invasive glucose sensor performance analysis method described herein includes obtaining a glucose reading using the minimally invasive glucose sensor, and comparing the glucose reading against a reference glucose reading that is obtained at generally the same time by a reference glucose sensor that transmits and receives sensing signals in a radio or microwave frequency range of the electromagnetic spectrum, where the reference glucose sensor has at least two antennas at least one of which operates as a transmit antenna to transmit one or more of the sensing signals and at least one of which operates as a receive antenna. In addition, an accuracy value, such as a MARD value, of the minimally invasive glucose sensor is generated based on the comparing of the glucose reading against the reference glucose reading.

DETAILED DESCRIPTION

The following is a detailed description of apparatus, systems and methods of detecting an analyte via spectroscopic techniques using non-optical frequencies such as in the radio or microwave frequency bands of the electromagnetic spectrum. An analyte sensor described herein includes a plurality of antennas or detector elements, at least one of which can transmit an electromagnetic signal in the radio or microwave frequency range into a target and at least one of which can receive an electromagnetic signal in the radio or microwave frequency range resulting from transmission of the electromagnetic signal. In an embodiment, the antennas may be part of a common antenna array. Further information on the construction and operation of analyte sensors are disclosed in U.S. Pat. Nos. 10,548,503; 11,063,373; 11,234,619; 11,031,970; 11,223,383; 11,058,317; 11,058,331; 11,193,923; 11,033,208; and U.S. Patent Application Publications 2021/0186357; 2021/0244308; 2021/0259571; 2021/0259592; 2021/0259593; 2022/0071523; 2022/0077918; 2022/0077602; 2022/0071527; 2022/0071505; 2022/0074870; 2022/0074871; 2022/0071524; each one of which is incorporated herein by reference in its entirety.

The analyte sensor described herein can be used to detect glucose and/or other analyte(s). When used to detect glucose, the sensor can be referred to as a glucose sensor. When used to detect an analyte in general, including glucose and other analytes, the sensor can be referred to as an analyte sensor. The sensor described herein can operate non-invasively whereby the sensor remains completely external to the body from which the glucose or other analyte(s) is sensed and the detection of the glucose or other analyte occurs without requiring removal of fluid or other removal from the target, such as the human body. In other embodiments, the sensor can operate in a minimally invasive manner whereby a portion of the sensor pierces the body, the sensor can be invasive whereby the sensor is completely installed in the body, or the sensor can sense glucose or other analyte(s) from a material or fluid that is drawn from and external to the body.

For sake of convenience, hereinafter the sensor will be described as sensing glucose and the sensor will be referred to as a glucose sensor. When used non-invasively, the glucose sensor described herein simultaneously obtains glucose readings from blood, interstitial fluid and cellular material which increases the accuracy of the glucose sensor compared to conventional glucose sensors, such as minimally invasive continuous glucose monitors (CGMs) and fingerstick sensors, which obtain glucose readings from one source, namely interstitial fluid in the case of minimally invasive CGMs and blood in the case of fingerstick sensors. However, in one embodiment, the glucose sensor described herein can be used to detect glucose from just blood, for example blood that has been drawn from a body; or from just interstitial fluid; from just cellular material; or from any two of these materials.

The glucose sensors described herein operate by transmitting an electromagnetic signal in the radio or microwave frequency range of the electromagnetic spectrum toward and into a target using a transmit antenna. A returning signal that results from the transmission of the transmitted signal is detected by a receive antenna. The signal(s) detected by the receive antenna can be analyzed to detect the analyte based on the intensity of the received signal(s) and reductions in intensity at one or more frequencies where the analyte absorbs the transmitted signal.

Figure 1:
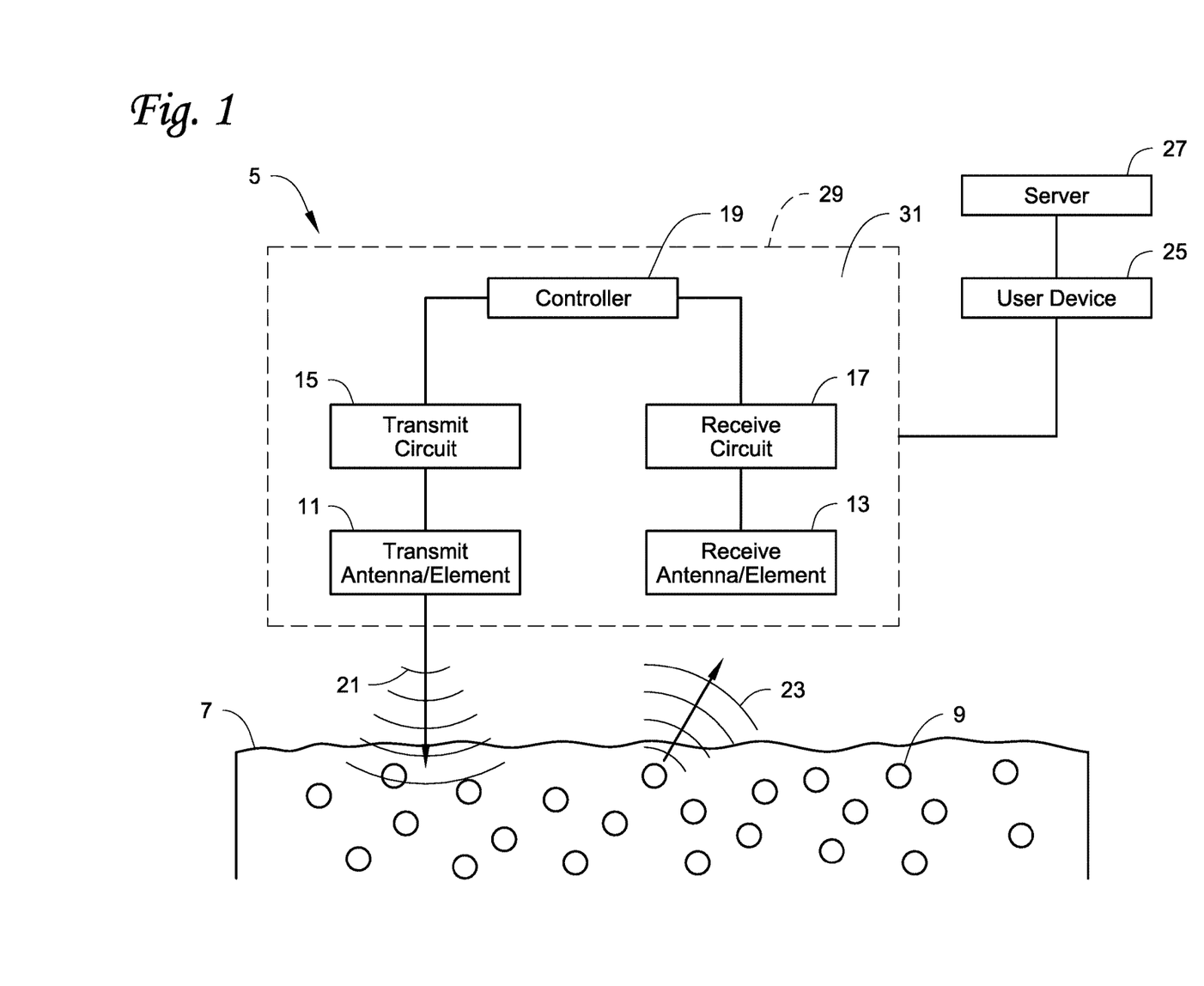
FIG. 1 is a schematic depiction of an analyte sensor system with an analyte sensor relative to a target according to an embodiment.

FIG. 1 illustrates the glucose sensor configured as a non-invasive glucose sensor that uses two or more antennas including one that functions as a transmit antenna and one that functions as a receive antenna. The transmit antenna and the receive antenna can be located near the target and operated as further described herein to assist in detecting glucose in the target. The transmit antenna transmits a signal toward and into the target. The receive antenna detects a response resulting from transmission of the signal by the transmit antenna into the target.

The transmit antenna and the receive antenna are decoupled (which may also be referred to as detuned or the like) from one another. Decoupling refers to intentionally fabricating the configuration and/or arrangement of the transmit antenna and the receive antenna to minimize direct communication between the transmit antenna and the receive antenna, preferably absent shielding. Shielding between the transmit antenna and the receive antenna can be utilized. However, the transmit antenna and the receive antenna are decoupled even without the presence of shielding.

Referring now to FIG. 1, an embodiment of a non-invasive glucose sensor system with a non-invasive glucose sensor 5 is illustrated. The sensor 5 is depicted relative to a target 7 from which the glucose 9 is to be detected. The glucose 9 can be in blood of the target 7, interstitial fluid of the target 7, and cellular material of the target 7. In this example, the sensor 5 is depicted as including an antenna array that includes a transmit antenna/element 11 (hereinafter "transmit antenna 11") and a receive antenna/element 13 (hereinafter "receive antenna 13"). The sensor 5 further includes a transmit circuit 15, a receive circuit 17, and a controller 19. The sensor 5 can also include a power supply, such as a battery (not shown in FIG. 1). In some embodiments, power can be provided from mains power, for example by plugging the sensor 5 into a wall socket via a cord connected to the sensor 5.

The transmit antenna 11 is positioned, arranged and configured to transmit a signal 21 that is in the radio frequency (RF) or microwave range of the electromagnetic spectrum into the target 7. The transmit antenna 11 can be an electrode or any other suitable transmitter of electromagnetic signals in the radio frequency (RF) or microwave range. The transmit antenna 11 can have any arrangement and orientation relative to the target 7 that is sufficient to allow the analyte sensing to take place. In one non-limiting embodiment, the transmit antenna 11 can be arranged to face in a direction that is substantially toward the target 7.

The signal 21 transmitted by the transmit antenna 11 is generated by the transmit circuit 15 which is electrically connectable to the transmit antenna 11. The transmit circuit 15 can have any configuration that is suitable to generate a transmit signal to be transmitted by the transmit antenna 11. Transmit circuits for generating transmit signals in the RF or microwave frequency range are well known in the art. In one embodiment, the transmit circuit 15 can include, for example, a connection to a power source, a frequency generator, and optionally filters, amplifiers or any other suitable elements for a circuit generating an RF or microwave frequency electromagnetic signal. In an embodiment, the signal generated by the transmit circuit 15 can have frequency that is in the range from about 10 kHz to about 100 GHz. In another embodiment, the frequency can be in a range from about 300 MHz to about 6000 MHz. In an embodiment, the transmit circuit 15 can be configured to sweep through a range of frequencies that are within the range of about 10 kHz to about 100 GHz, or in another embodiment a range of about 300 MHz to about 6000 MHz.

The receive antenna 13 is positioned, arranged, and configured to detect one or more electromagnetic response signals 23 that result from the transmission of the transmit signal 21 by the transmit antenna 11 into the target 7 and impinging on the glucose molecules 9. The receive antenna 13 can be an electrode or any other suitable receiver of electromagnetic signals in the radio frequency (RF) or microwave range. In an embodiment, the receive antenna 13 is configured to detect electromagnetic signals having a frequency that is in the range from about 10 kHz to about 100 GHz, or in another embodiment a range from about 300 MHz to about 6000 MHz. The receive antenna 13 can have any arrangement and orientation relative to the target 7 that is sufficient to allow detection of the response signal(s) 23 to allow the glucose sensing to take place. In one non-limiting embodiment, the receive antenna 13 can be arranged to face in a direction that is substantially toward the target 7.

The receive circuit 17 is electrically connectable to the receive antenna 13 and conveys the received response from the receive antenna 13 to the controller 19. The receive circuit 17 can have any configuration that is suitable for interfacing with the receive antenna 13 to convert the electromagnetic energy detected by the receive antenna 13 into one or more signals reflective of the response signal(s) 23. The construction of receive circuits are well known in the art. The receive circuit 17 can be configured to condition the signal(s) prior to providing the signal(s) to the controller 19, for example through amplifying the signal(s), filtering the signal(s), or the like. Accordingly, the receive circuit 17 may include filters, amplifiers, or any other suitable components for conditioning the signal(s) provided to the controller 19.

The controller 19 controls the operation of the sensor 5. The controller 19, for example, can direct the transmit circuit 15 to generate a transmit signal to be transmitted by the transmit antenna 11. The controller 19 further receives signals from the receive circuit 17. The controller 19 can optionally process the signals from the receive circuit 17 to detect the analyte(s) 9 in the target 7. In one embodiment, the controller 19 may optionally be in communication with at least one external device 25 such as a user device and/or a remote server 27, for example through one or more wireless connections such as Bluetooth, wireless data connections such a 4G, 5G, LTE or the like, or Wi-Fi. If provided, the external device 25 and/or remote server 27 may process (or further process) the signals that the controller 19 receives from the receive circuit 17, for example to detect the glucose molecules 9. If provided, the external device 25 may be used to provide communication between the sensor 5 and the remote server 27, for example using a wired data connection or via a wireless data connection or Wi-Fi of the external device 25 to provide the connection to the remote server 27.

With continued reference to FIG. 1, the sensor 5 may include a sensor housing 29 (shown in dashed lines) that defines an interior space 31. Components of the sensor 5 may be attached to and/or disposed within the housing 29. For example, the transmit antenna 11 and the receive antenna 13 are attached to the housing 29. In some embodiments, the antennas 11, 13 may be entirely or partially within the interior space 31 of the housing 29. In some embodiments, the antennas 11, 13 may be attached to the housing 29 but at least partially or fully located outside the interior space 31. In some embodiments, the transmit circuit 15, the receive circuit 17 and the controller 19 are attached to the housing 29 and disposed entirely within the sensor housing 29.

The receive antenna 13 is decoupled or detuned with respect to the transmit antenna 11 such that electromagnetic coupling between the transmit antenna 11 and the receive antenna 13 is reduced. The decoupling of the transmit antenna 11 and the receive antenna 13 increases the portion of the signal(s) detected by the receive antenna 13 that is the response signal(s) 23 from the target 7, and minimizes direct receipt of the transmitted signal 21 by the receive antenna 13. The decoupling of the transmit antenna 11 and the receive antenna 13 results in transmission from the transmit antenna 11 to the receive antenna 13 having a reduced forward gain ($S_{21}$) and an increased reflection at output ($S_{22}$) compared to antenna systems having coupled transmit and receive antennas.

In an embodiment, coupling between the transmit antenna 11 and the receive antenna 13 is 95% or less. In another embodiment, coupling between the transmit antenna 11 and the receive antenna 13 is 90% or less. In another embodiment, coupling between the transmit antenna 11 and the receive antenna 13 is 85% or less. In another embodiment, coupling between the transmit antenna 11 and the receive antenna 13 is 75% or less.

Any technique for reducing coupling between the transmit antenna 11 and the receive antenna 13 can be used. For example, the decoupling between the transmit antenna 11 and the receive antenna 13 can be achieved by one or more intentionally fabricated configurations and/or arrangements between the transmit antenna 11 and the receive antenna 13 that is sufficient to decouple the transmit antenna 11 and the receive antenna 13 from one another.

For example, in one embodiment described further below, the decoupling of the transmit antenna 11 and the receive antenna 13 can be achieved by intentionally configuring the transmit antenna 11 and the receive antenna 13 to have different geometries from one another. Intentionally different geometries refers to different geometric configurations of the transmit and receive antennas 11, 13 that are intentional. Intentional differences in geometry are distinct from differences in geometry of transmit and receive antennas that may occur by accident or unintentionally, for example due to manufacturing errors or tolerances.

Another technique to achieve decoupling of the transmit antenna 11 and the receive antenna 13 is to provide appropriate spacing between each antenna 11, 13 that is sufficient to decouple the antennas 11, 13 and force a proportion of the electromagnetic lines of force of the transmitted signal 21 into the target 7 thereby minimizing or eliminating as much as possible direct receipt of electromagnetic energy by the receive antenna 13 directly from the transmit antenna 11 without traveling into the target 7. The appropriate spacing between each antenna 11, 13 can be determined based upon factors that include, but are not limited to, the output power of the signal from the transmit antenna 11, the size of the antennas 11, 13, the frequency or frequencies of the transmitted signal, and the presence of any shielding between the antennas. This technique helps to ensure that the response detected by the receive antenna 13 is measuring the glucose molecules 9 and is not just the transmitted signal 21 flowing directly from the transmit antenna 11 to the receive antenna 13. In some embodiments, the appropriate spacing between the antennas 11, 13 can be used together with the intentional difference in geometries of the antennas 11, 13 to achieve decoupling.

In one embodiment, the transmit signal (or each of the transmit signals) can be transmitted over a transmit time that is less than, equal to, or greater than about 300 ms. In another embodiment, the transmit time can be less than, equal to, or greater than about 200 ms. In still another embodiment, the transmit time can be less than, equal to, or greater than about 30 ms. The transmit time could also have a magnitude that is measured in seconds, for example 1 second, 5 seconds, 10 seconds, or more. In an embodiment, the same transmit signal can be transmitted multiple times, and then the transmit time can be averaged. In another embodiment, the transmit signal (or each of the transmit signals) can be transmitted with a duty cycle that is less than or equal to about 50%.

As mentioned above, one technique for decoupling the transmit antenna 11 from the receive antenna 13 is to intentionally configure the transmit antenna 11 and the receive antenna 13 to have intentionally different geometries. Intentionally different geometries refers to differences in geometric configurations of the transmit and receive antennas 11, 13 that are intentional, and is distinct from differences in geometry of the transmit and receive antennas 11, 13 that may occur by accident or unintentionally, for example due to manufacturing errors or tolerances when fabricating the antennas 11, 13.

The different geometries of the antennas 11, 13 may manifest itself, and may be described, in a number of different ways. For example, in a plan view of each of the antennas 11, 13 (such as in FIGS. 2A-C), the shapes of the perimeter edges of the antennas 11, 13 may be different from one another. The different geometries may result in the antennas 11, 13 having different surface areas in plan view. The different geometries may result in the antennas 11, 13 having different aspect ratios in plan view (i.e. a ratio of their sizes in different dimensions; for example, as discussed in further detail below, the ratio of the length divided by the width of the antenna 11 may be different than the ratio of the length divided by the width for the antenna 13). In some embodiments, the different geometries may result in the antennas 11, 13 having any combination of different perimeter edge shapes in plan view, different surface areas in plan view, and/or different aspect ratios.

So as used herein, a difference in geometry or a difference in geometrical shape of the antennas 11, 13 refers to any intentional difference in the figure, length, width, size, shape, area closed by a boundary (i.e. the perimeter edge), etc. when the respective antenna 11, 13 is viewed in a plan view.

The antennas 11, 13 can have any configuration and can be formed from any suitable material that allows them to perform the functions of the antennas 11, 13 as described herein. In one embodiment, the antennas 11, 13 can be formed by strips of material. A strip of material can include a configuration where the strip has at least one lateral dimension thereof greater than a thickness dimension thereof when the antenna is viewed in a plan view (in other words, the strip is relatively flat or of relatively small thickness compared to at least one other lateral dimension, such as length or width when the antenna is viewed in a plan view as in FIGS. 2A-C). A strip of material can include a wire. The antennas 11, 13 can be formed from any suitable conductive material(s) including metals and conductive non-metallic materials. Examples of metals that can be used include, but are not limited to, copper or gold. Another example of a material that can be used is non-metallic materials that are doped with metallic material to make the non-metallic material conductive.

Figure 2A:
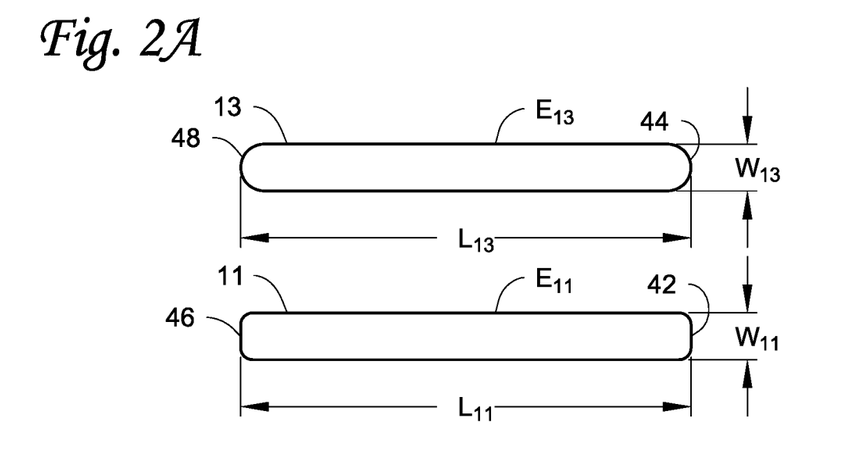
FIGS. 2A-2C illustrate different examples of transmit and receive antennas with different geometries.

FIG. 2A illustrates a plan view of an antenna array having two antennas with different geometries. In this example, the antennas 11, 13 are illustrated as substantially linear strips. In this example, the antennas 11, 13 differ in geometry from one another in that the shapes of the ends of the antennas 11, 13 differ from one another. For example, when viewing FIG. 2A, the right end 42 of the antenna 11 has a different shape than the right end 44 of the antenna 13. Similarly, the left end 46 of the antenna 11 may have a similar shape as the right end 42, but differs from the left end 48 of the antenna 13 which may have a similar shape as the right end 44. It is also possible that the lateral lengths $L_{11}$, $L_{13}$ and/or the lateral widths $W_{11}$, $W_{13}$ of the antennas 11, 13 could differ from one another.

Figure 2B:
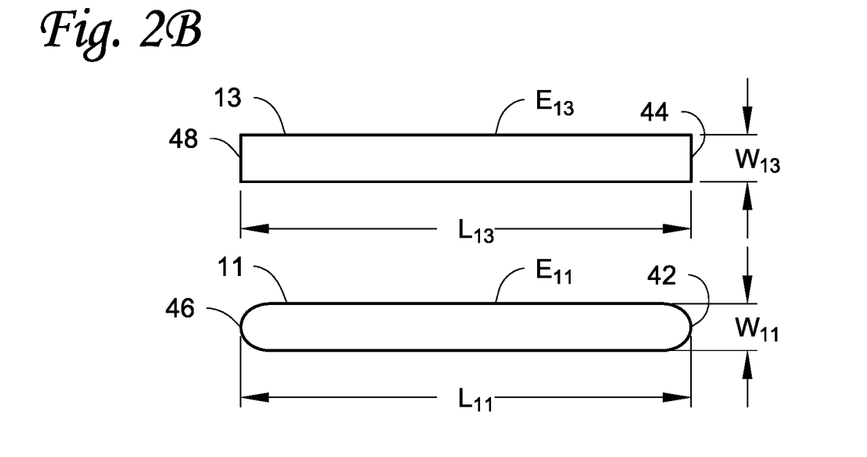

FIG. 2B illustrates another plan view of an antenna array having two antennas with different geometries that is somewhat similar to FIG. 2A. In this example, the antennas 11, 13 are illustrated as substantially linear strips, and the antennas 11, 13 differ in geometry from one another in that the shapes of the ends of the antennas 11, 13 differ from one another. For example, when viewing FIG. 2B, the right end 42 of the antenna 11 has a different shape than the right end 44 of the antenna 13. Similarly, the left end 46 of the antenna 11 may have a similar shape as the right end 42, but differs from the left end 48 of the antenna 13 which may have a similar shape as the right end 44. In addition, the lateral widths $W_{11}$, $W_{13}$ of the antennas 11, 13 differ from one another. It is also possible that the lateral lengths $L_{11}$, $L_{13}$ of the antennas 11, 13 could differ from one another.

Figure 2C:
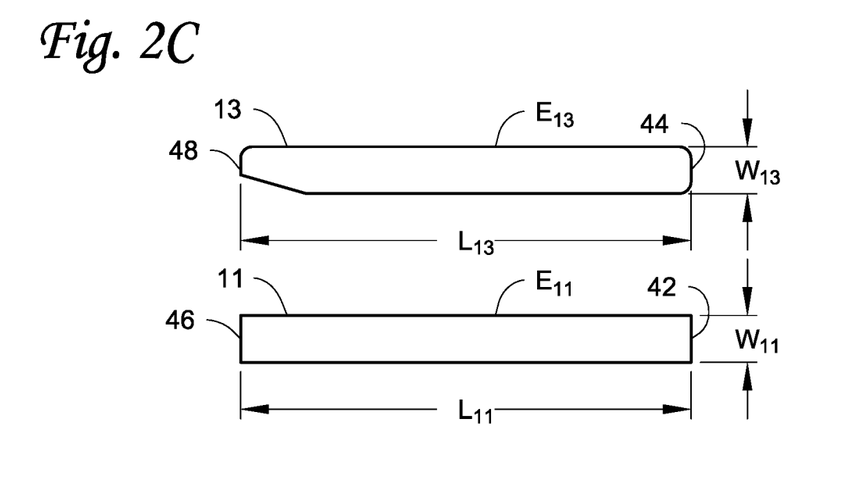

FIG. 2C illustrates another plan view of an antenna array having two antennas with different geometries that is somewhat similar to FIGS. 2A and 2B. In this example, the antennas 11, 13 are illustrated as substantially linear strips, and the antennas 11, 13 differ in geometry from one another in that the shapes of the ends of the antennas 11, 13 differ from one another. For example, when viewing FIG. 2C, the right end 42 of the antenna 11 has a different shape than the right end 44 of the antenna 13. Similarly, the left end 46 of the antenna 11 may have a similar shape as the right end 42, but differs from the left end 48 of the antenna 13 which may have a similar shape as the right end 44. In addition, the lateral widths $W_{11}$, $W_{13}$ of the antennas 11, 13 differ from one another. It is also possible that the lateral lengths $L_{11}$, $L_{13}$ of the antennas 11, 13 could differ from one another.

Figure 3:
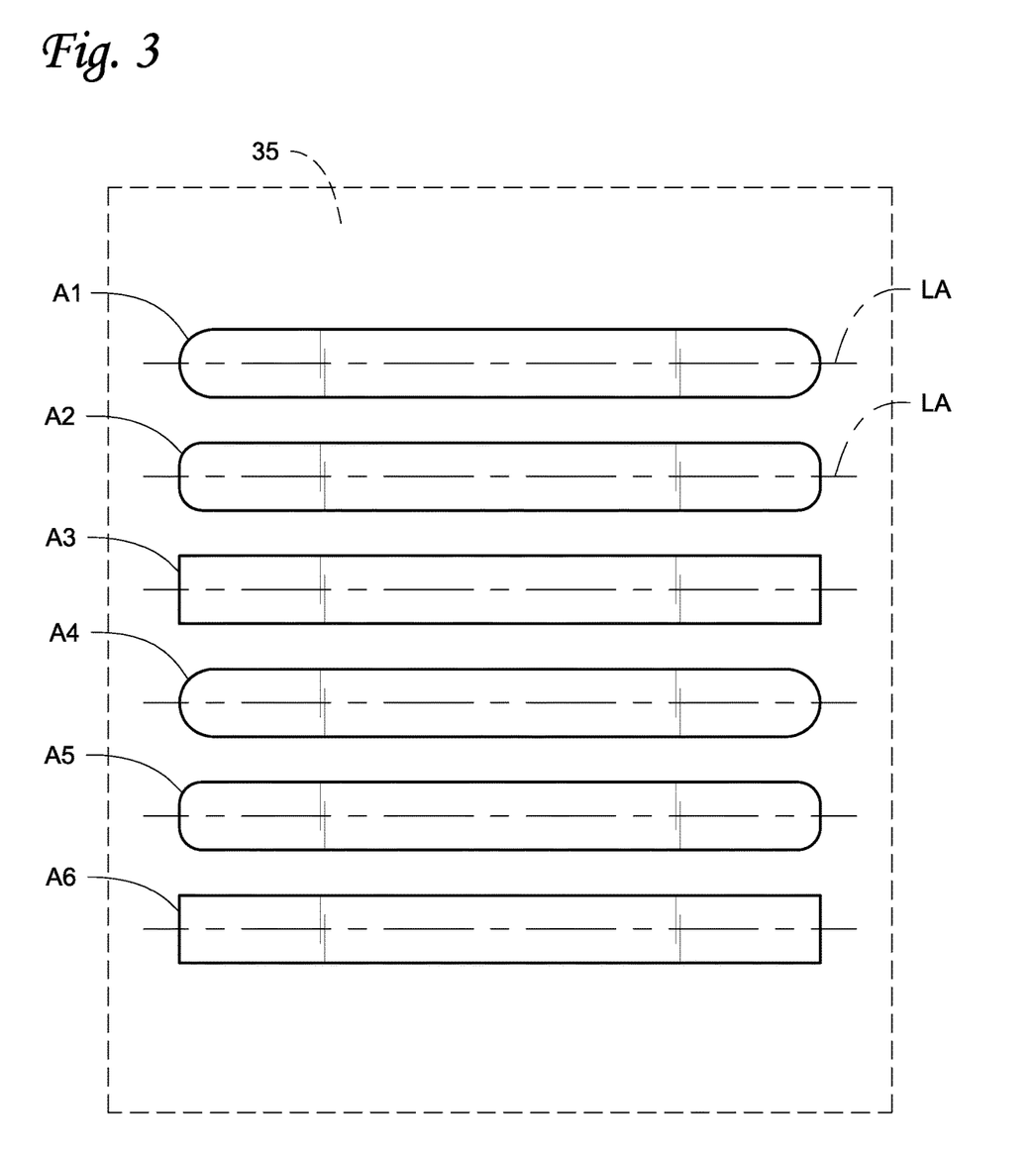
FIG. 3 illustrates another example of an antenna array that can be used.

The examples in FIGS. 1 and 2A-C depict the use of two antennas. However, a different number of antennas can be used, as long as at least one of the antennas can function as a transmit antenna and as long as at least one of the antennas can function as a receive antenna. FIG. 3 illustrates a plan view of an antenna array having six antennas illustrated as substantially linear strips. In this example, the antennas differ in geometry from one another in that the shapes of the ends of the antennas, the lateral lengths and/or the lateral widths of the antennas may differ from one another. However, in one embodiment three antennas can be used, four antennas can be used, five antennas can be used, etc.

Referring to FIG. 3, the antennas are labeled in order A1-A6. Each antenna A1-A6 can function as either a transmit antenna or as a receive antenna. In another embodiment, each antenna A1-A6 can operate solely as a transmit antenna or as a receive antenna. All of the antennas A1-A6 are depicted as being disposed on the same substrate 35. However, the antennas A1-A6 can be disposed on two or more substrates. In addition, each one of the antennas A1-A6 has a longitudinal axis LA (depicted in dashed lines), and the longitudinal axes LA of the antennas A1-A6 are illustrated as being parallel to each other. However, the longitudinal axes LA need not be parallel. Some of the longitudinal axes may be parallel to one another while others are angled; or all of the longitudinal axes may be angled (i.e. not parallel to one another).

Further, at least one of the antennas A1-A6 has a rectangular shape, at least one of the antennas A1-A6 has a stadium shape, and at least one of the antennas A1-A6 has a rounded rectangle shape. In the illustrated embodiment, two of the antennas, such as the antennas A3 and A6, have a rectangular shape; two of the antennas, such as the antennas A1 and A4, have a stadium shape; and two of the antennas, such as the antennas A2 and A5, have a rounded rectangle shape. A stadium shape is a two-dimensional geometric shape constructed of a rectangle with semicircles at opposite ends. A rounded rectangle shape is a two-dimensional geometric shape constructed of a rectangle with radiuses at each corner of the rectangle. The antennas in FIG. 3 are arranged on the substrate 35 in a manner such that two antennas with the same shape are not located next to one another.

The antenna array in FIG. 3 is configured such that a first one of the antennas, such as the antenna A1 or A4, has a first perimeter length; a second one of the antennas, such as the antenna A2 or A5, has a second perimeter length; and a third one of the antennas, such as the antenna A3 or A6, has a third perimeter length. In one embodiment, the first perimeter length, the second perimeter length, and the third perimeter length differ from one another. The difference in perimeter lengths is due to the different geometric shapes of the antennas. In another embodiment, the antennas A1-A6 can have different geometric shapes but some or all of the perimeter lengths of the antennas A1-A6 can be the same. In still another embodiment, the antennas A1-A6 can have the same geometric shape but different perimeter lengths. In one embodiment, each antenna A1-A6 can have the same maximum longitudinal length L and the same maximum width W, with the different geometrical shapes accounting for the different perimeter lengths.

The glucose sensor described herein is highly accurate. One way to assess the accuracy of a glucose sensor is known as MARD. A MARD value of a glucose sensor is determined by comparing the glucose reading of the glucose sensor against a reference glucose reading of a reference glucose sensor. The lower the MARD value, the more accurate the glucose sensor is. For example, the MARD value can be determined as follows:

$$ARD_k = 100\% \times \frac{|ygs(tk) - Yref(tk)|}{yref(tk)}$$

$$MARD = \frac{1}{Nref} \sum_{k=1}^{Nref} ARDk$$

where: $y_{gs}$ is the value measured by the glucose sensor described herein at time $t_k$;

$y_{ref}$ is the value measured by the reference glucose sensor at time $t_k$;

$t_k$, k=1, 2, . . . $N_{ref}$ are the times when the reference measurements are taken.

For example, the glucose sensor described herein has a MARD value of between about 5.0% to about 9.9%, or the MARD value is between about 5.0% to about 7%, or the MARD value is about 5.0%. The MARD value of the sensor described herein is based on a comparison between one or more glucose readings obtained by the glucose sensor described herein with one or more glucose readings contemporaneously obtained by a fingerstick sensor or by a minimally invasive continuous glucose sensor as the reference sensor. Applicant believes that a MARD value of between about 5.0% to about 9.9% would also be obtained by the glucose sensor described herein when compared to a reference value determined by a YSI glucose analyzer.

The non-invasive glucose sensor described herein has an accuracy that is greater than an accuracy of commercially available glucose sensors such as minimally invasive continuous glucose sensor and fingerstick glucose sensor. Examples of minimally invasive continuous glucose sensors are, but are not limited to, the FreeStyle Libre® CGM, the Dexcom® G6, and many others. An example of a fingerstick glucose sensor includes, but is not limited to, a OneTouch® Ultra®2. The Dexcom G6 has a MARD value of around 9%, and the FreeStyle Libre has a MARD value of around 9.3% each of which is determined compared to a reference value determined by a YSI glucose analyzer. The OneTouch Ultra2 has a reported MARD value that ranges from around 16.7 to about 30.1 which is determined compared to a reference value determined by a YSI glucose analyzer.

There may be a number of reasons why the non-invasive glucose sensor described herein has a high accuracy. One reason for the high accuracy of the glucose sensor described herein is believed to be that the sensor simultaneously obtains glucose readings from blood, interstitial fluid and cellular material. Conventional glucose sensors, such as minimally invasive continuous glucose monitors (CGMs) and fingerstick sensors, obtain glucose readings from one source, namely interstitial fluid in the case of minimally invasive CGMs and blood in the case of fingerstick sensors. Accordingly, the glucose sensor transmits and receives sensing signals in a radio or microwave frequency range of the electromagnetic spectrum, with the glucose sensor having at least two antennas at least one of which operates as a transmit antenna to transmit one or more of the sensing signals and at least one of which operates as a receive antenna, and the glucose sensor simultaneously detects glucose from blood, interstitial fluid, and cellular material.

Additional reasons for the high accuracy of the glucose sensor described herein are believed to be, but are not necessarily limited to, the control of frequency sweeps as described in U.S. Pat. No. 11,033,208, the entire contents of which are incorporated herein by reference in their entirety; the ability to use different combinations of transmit and receive antennas as described in U.S. Pat. No. 11,058,331, the entire contents of which are incorporated herein by reference in their entirety; and the use of different antenna geometries as described herein.

The high accuracy of the non-invasive glucose sensor described herein, when compared to lower accuracy glucose sensors such as minimally invasive CGMs and fingerstick glucose sensors, means that the non-invasive glucose sensor described herein can be used as a standard or reference sensor against which the accuracy of other glucose sensors are gauged. In one embodiment, readings from the non-invasive glucose sensor described herein can be used in place of readings obtained by a YSI glucose analyzer.

Figure 4:
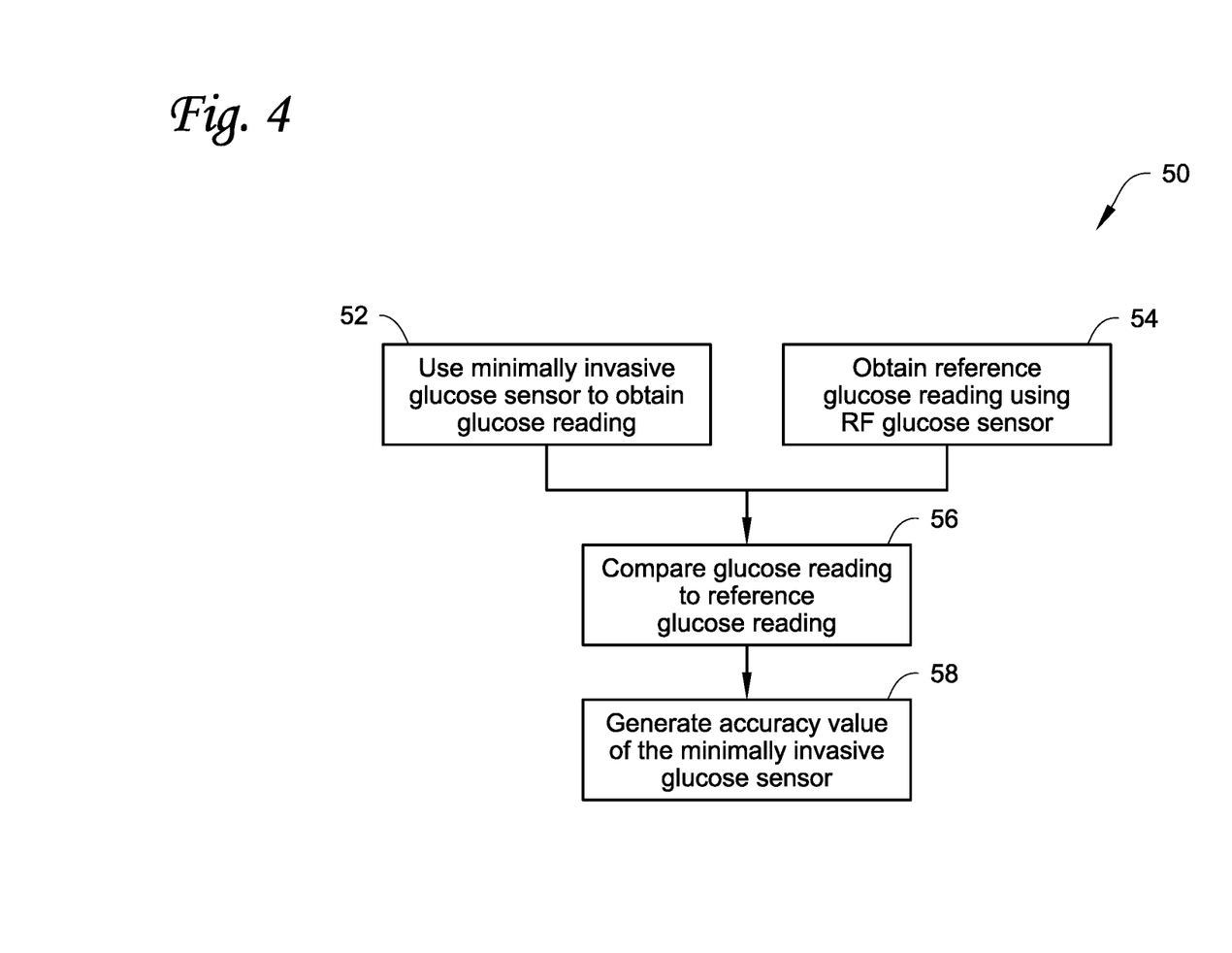
FIG. 4 is a schematic depiction of a method of using the analyte sensor described herein as a reference or standard glucose sensor against which the performance of other glucose sensors can be compared to determine their accuracy.

Referring to FIG. 4, an example of using the non-invasive glucose sensor described herein as a reference sensor is illustrated. FIG. 4 schematically depicts a method 50 of using the analyte sensor described herein as a reference or standard glucose sensor against which the accuracy of a minimally invasive glucose sensor, such as a minimally invasive CGM, is determined. At 52, a glucose reading is obtained using the minimally invasive glucose sensor. Contemporaneously, at 54, a reference glucose reading is obtained using the radio/microwave frequency glucose sensor described herein. At 56, the glucose reading from the minimally invasive glucose sensor is compared against the reference glucose reading that is obtained at 54. For example, the comparison could be done in order to determine the MARD value of the minimally invasive glucose sensor as described above. At 58, an accuracy value of the minimally invasive glucose sensor is then determined based on the comparison at 56.

The glucose sensor described herein can be considered continuous in that it operates substantially continuously to obtain multiple glucose readings over an extended period of time. In another embodiment, the glucose sensor described herein can be considered "on-demand" whereby a user initiates a reading or readings.

The examples disclosed in this application are to be considered in all respects as illustrative and not limitative. The scope of the invention is indicated by the appended claims rather than by the foregoing description; and all changes which come within the meaning and range of equivalency of the claims are intended to be embraced therein.

The invention claimed is:

1. A glucose sensor that transmits and receives sensing signals in a radio or microwave frequency range of the electromagnetic spectrum, the glucose sensor having at least two antennas at least one of which is operable as a transmit antenna to transmit one or more of the sensing signals and at least one of which is operable as a receive antenna, and the glucose sensor has a mean absolute relative difference (MARD) value of about 5.0% to about 9.9% as compared with a reference glucose reading from a reference glucose sensor based on a plurality of readings by the glucose sensor,
wherein the glucose sensor is configured to simultaneously detect glucose from blood and interstitial fluid.

2. The glucose sensor of claim 1, wherein the MARD value is about 5.0% to about 7.0%.

3. The glucose sensor of claim 1, wherein the MARD value is about 5.0%.

4. The glucose sensor of claim 1, wherein the glucose sensor additionally simultaneously detects glucose from cellular material.

5. The glucose sensor of claim 1, wherein the glucose sensor is a continuous glucose sensor or an on-demand glucose sensor.

6. The glucose sensor of claim 1, wherein the at least two antennas are part of an antenna array;
a transmit circuit that is electrically connectable to the at least one transmit antenna, the transmit circuit is configured to generate the signals to be transmitted by the at least one transmit antenna; and
a receive circuit that is electrically connectable to the at least one receive antenna, the receive circuit is configured to receive responses detected by the at least one receive antenna.

7. The glucose sensor of claim 1, wherein the glucose sensor has at least three antennas.

8. The glucose sensor of claim 1, wherein the glucose sensor has at least four antennas.

9. The glucose sensor of claim 1, wherein the glucose sensor has at least six antennas.

10. The glucose sensor of claim 1, wherein each of the at least two antennas have a longitudinal axis parallel to one another, and one of the at least two antennas has a longitudinal end that has a different shape than a longitudinal end of another of the at least two antennas.

11. The glucose sensor of claim 8, wherein the at least four antennas each have a longitudinal axis parallel to one another, and at least one of the at least four antennas has a stadium shape, and at least one of the at least four antennas has a rounded rectangle shape.

12. The glucose sensor of claim 8, wherein at least one of the at least four antennas has a different perimeter length than remaining antennas of the at least four antennas.

13. A non-invasive glucose sensor that transmits and receives sensing signals in a radio or microwave frequency range of the electromagnetic spectrum to detect glucose in a human or animal body, the non-invasive glucose sensor having at least three antennas at least one of which is operable as a transmit antenna to transmit one or more of the sensing signals into the human or animal body and at least one of which is operable as a receive antenna, and the glucose sensor has a mean absolute relative difference (MARD) value of about 5.0% to about 7.0% as compared with a reference glucose reading from a reference glucose sensor based on a plurality of readings by the glucose sensor,
wherein the at least three antennas each have a longitudinal axis parallel to one another, and each of the at least three antennas comprises linear sides connected to longitudinal ends, and the longitudinal ends of at least one of the at least three antennas has different geometries from the longitudinal ends of the other of the at least three antennas.

14. The non-invasive glucose sensor of claim 13, wherein the MARD value is about 5.0%.

15. The non-invasive glucose sensor of claim 13, wherein the non-invasive glucose sensor simultaneously detects glucose from blood and interstitial fluid.

16. The non-invasive glucose sensor of claim 13, wherein the non-invasive glucose sensor is a continuous glucose sensor or an on-demand glucose sensor.

17. The non-invasive glucose sensor of claim 13, wherein the at least three antennas are part of an antenna array.

18. The non-invasive glucose sensor of claim 17, wherein the antenna array has at least four antennas.

19. The non-invasive glucose sensor of claim 17, wherein the antenna array has at least six antennas.

* * * * *